United States Patent
Brown et al.

(10) Patent No.: US 6,981,986 B1
(45) Date of Patent: Jan. 3, 2006

(54) LONGITUDINALLY FLEXIBLE EXPANDABLE STENT

(75) Inventors: Brian J. Brown, Hanover, MN (US); Michael L. Davis, Shorewood, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 09/666,866

(22) Filed: Sep. 20, 2000

Related U.S. Application Data

(63) Continuation of application No. 09/122,431, filed on Jul. 24, 1998, now Pat. No. 6,348,065, which is a continuation of application No. 08/511,076, filed on Aug. 3, 1995, now Pat. No. 6,818,014, which is a continuation-in-part of application No. 08/396,569, filed on Mar. 1, 1995, now abandoned.

(51) Int. Cl.
*A61F 2/06* (2006.01)
(52) U.S. Cl. ..................... 623/1.16; 623/23.7
(58) Field of Classification Search ................ 606/151, 606/191, 192, 194, 195; 623/1.15, 1.16, 623/1.17, 1.13, 23.7, 1.18
See application file for complete search history.

(56) References Cited

U.S. PATENT DOCUMENTS

| | | | |
|---|---|---|---|
| 2,836,181 A | 5/1958 | Tapp | |
| 3,105,492 A | 10/1963 | Jeckel | |
| 3,272,204 A | 9/1966 | Artandi et al. | |
| 3,490,975 A | 1/1970 | Lightwood et al. | |
| 3,509,883 A | 5/1970 | Dibelius | |
| 3,526,228 A | 9/1970 | Lyng | |
| 3,562,820 A | 2/1971 | Braun | |
| 3,635,215 A | 1/1972 | Shea et al. | |
| 3,657,744 A | 4/1972 | Ersek | |
| 3,771,526 A | 11/1973 | Rudle | |
| 3,868,956 A | 3/1975 | Alfidi et al. | |
| 3,993,078 A | 11/1976 | Bergentz et al. | |
| 4,078,167 A | 3/1978 | Banas et al. | |
| 4,127,761 A | 11/1978 | Pauley et al. | |
| 4,130,904 A | 12/1978 | Whalen | |
| 4,140,126 A | 2/1979 | Choudhury | |
| 4,141,364 A | 2/1979 | Schultze | |
| 4,164,045 A | 8/1979 | Bokros et al. | |

(Continued)

FOREIGN PATENT DOCUMENTS

EP  0 364 787 B1  4/1990

(Continued)

OTHER PUBLICATIONS

*Manufacturing Processes for Engineering Materials*, by Serope Kalpakjian, Illinois Institute of Technology, Addison-Wesley Publishing Company, pp. 340.

(Continued)

*Primary Examiner*—Paul B. Prebilic
(74) *Attorney, Agent, or Firm*—Vidas, Arrett, Steinkraus

(57) ABSTRACT

A stent in a non-expanded state includes a first expansion column and a second expansion column. The first expansion column comprises a plurality of expansion strut pairs. Each expansion strut pair includes a first expansion strut and a second expansion strut joined by a joining strut. The second expansion column comprises a plurality of expansion strut pairs. Each expansion strut pair includes a first expansion strut and a second expansion strut joined by a joining strut. The first and second expansion columns are connected via a first connecting strut column. The first connecting strut column comprises a plurality of first connecting struts. The first expansion strut of the first expansion strut pair in the first expansion column has a longitudinal axis offset from a longitudinal axis of the first expansion strut of the second expansion strut pair in the second expansion column.

19 Claims, 3 Drawing Sheets

U.S. PATENT DOCUMENTS

| | | |
|---|---|---|
| 4,214,587 A | 7/1980 | Sakura, Jr. |
| 4,300,244 A | 11/1981 | Bokros |
| 4,313,231 A | 2/1982 | Koyamada |
| 4,319,363 A | 3/1982 | Ketharanathan |
| 4,425,908 A | 1/1984 | Simon |
| 4,441,215 A | 4/1984 | Kaster |
| 4,470,407 A | 9/1984 | Hussein |
| 4,501,264 A | 2/1985 | Rockey |
| 4,503,569 A | 3/1985 | Dotter |
| 4,512,338 A | 4/1985 | Balko et al. |
| 4,535,770 A | 8/1985 | Lemole |
| 4,550,447 A | 11/1985 | Seiler, Jr. et al. |
| 4,553,545 A | 11/1985 | Maass et al. |
| 4,560,374 A | 12/1985 | Hammerslag |
| 4,580,568 A | 4/1986 | Gianturco |
| 4,597,389 A | 7/1986 | Ibrahim et al. |
| 4,647,416 A | 3/1987 | Seiler, Jr. et al. |
| 4,649,922 A | 3/1987 | Wiktor |
| 4,655,771 A | 4/1987 | Wallsten |
| 4,655,776 A | 4/1987 | Lesinski |
| 4,665,906 A | 5/1987 | Jervis .......................... 128/92 |
| 4,665,918 A | 5/1987 | Garza et al. |
| 4,681,110 A | 7/1987 | Wiktor |
| 4,693,721 A | 9/1987 | Ducheyne |
| 4,733,665 A | 3/1988 | Palmaz |
| 4,739,762 A | 4/1988 | Palmaz |
| 4,740,207 A | 4/1988 | Kreamer |
| 4,760,849 A | 8/1988 | Kropf |
| 4,762,128 A | 8/1988 | Rosenbluth |
| 4,769,029 A | 9/1988 | Patel |
| 4,771,773 A | 9/1988 | Kropf |
| 4,776,337 A | 10/1988 | Palmaz |
| 4,786,507 A | 11/1988 | Schmidt |
| 4,787,899 A | 11/1988 | Lazarus |
| 4,795,458 A | 1/1989 | Regan |
| 4,795,465 A | 1/1989 | Marten |
| 4,800,882 A | 1/1989 | Gianturco |
| 4,820,298 A | 4/1989 | Leveen et al. |
| 4,830,003 A | 5/1989 | Wolff et al. |
| 4,842,575 A | 6/1989 | Hoffman, Jr. et al. |
| 4,848,343 A | 7/1989 | Wallsten et al. |
| 4,851,009 A | 7/1989 | Pinchuk |
| 4,856,516 A | 8/1989 | Hillstead |
| 4,872,874 A | 10/1989 | Taheri |
| 4,877,030 A | 10/1989 | Beck et al. |
| 4,878,906 A | 11/1989 | Lindemann et al. |
| 4,886,062 A | 12/1989 | Wiktor |
| 4,913,141 A | 4/1990 | Hillstead |
| 4,922,905 A | 5/1990 | Strecker |
| 4,950,227 A | 8/1990 | Savin et al. |
| 4,950,258 A | 8/1990 | Kawai et al. |
| 4,994,071 A | 2/1991 | MacGregor |
| 5,015,253 A | 5/1991 | MacGregor |
| 5,019,090 A | 5/1991 | Pinchuk |
| 5,035,706 A | 7/1991 | Gianturco et al. |
| 5,037,392 A | 8/1991 | Hillstead |
| 5,059,211 A | 10/1991 | Stack et al. |
| 5,064,435 A | 11/1991 | Porter |
| 5,071,407 A | 12/1991 | Termin et al. |
| 5,089,005 A | 2/1992 | Harada |
| 5,092,877 A | 3/1992 | Pinchuk |
| 5,102,417 A | 4/1992 | Palmaz |
| 5,104,399 A | 4/1992 | Lazarus |
| 5,104,404 A | 4/1992 | Wolff |
| 5,108,415 A | 4/1992 | Pinchuk et al. |
| 5,108,417 A | 4/1992 | Sawyer |
| 5,122,154 A | 6/1992 | Rhodes |
| 5,133,732 A | 7/1992 | Wiktor |
| 5,135,536 A | 8/1992 | Hillstead |
| 5,139,480 A | 8/1992 | Hickle et al. |
| 5,147,385 A | 9/1992 | Beck et al. |
| 5,147,400 A | 9/1992 | Kaplan et al. |
| 5,158,548 A | 10/1992 | Lau et al. |
| 5,163,952 A | 11/1992 | Froix |
| 5,195,984 A | 3/1993 | Schatz |
| 5,197,978 A | 3/1993 | Hess |
| 5,217,483 A | 6/1993 | Tower |
| 5,226,913 A | 7/1993 | Pinchuk |
| 5,282,823 A | 2/1994 | Schwartz et al. |
| 5,282,824 A | 2/1994 | Gianturco |
| 5,292,331 A | 3/1994 | Boneau |
| 5,304,121 A * | 4/1994 | Sahatjian .................... 604/509 |
| 5,304,200 A | 4/1994 | Spaulding |
| 5,344,425 A | 9/1994 | Sawyer |
| 5,354,308 A | 10/1994 | Simon et al. |
| 5,354,309 A | 10/1994 | Schnepp-Pesch et al. |
| 5,356,423 A | 10/1994 | Tihon et al. |
| 5,383,892 A | 1/1995 | Cardon et al. |
| 5,389,106 A | 2/1995 | Tower ........................ 606/198 |
| 5,405,377 A | 4/1995 | Cragg |
| 5,449,373 A | 9/1995 | Pinchasik et al. |
| 5,527,354 A | 6/1996 | Fontaine et al. ............... 623/1 |
| 5,545,210 A | 8/1996 | Hess et al. ..................... 623/1 |
| 5,549,663 A | 8/1996 | Cottone, Jr. ................... 623/1 |
| 5,554,181 A | 9/1996 | Das |
| 5,591,197 A | 1/1997 | Orth et al. ..................... 623/1 |
| 5,630,829 A | 5/1997 | Lauterjung |
| 5,643,312 A | 7/1997 | Fischell et al. |
| 5,653,727 A | 8/1997 | Wiktor ...................... 606/195 |
| 5,697,971 A | 12/1997 | Fischell et al. ................ 623/1 |
| 5,707,386 A | 1/1998 | Schnepp-Pesch et al. |
| 5,716,365 A | 2/1998 | Goicoechea et al. ........ 606/108 |
| 5,716,393 A | 2/1998 | Lindenberg et al. ......... 623/1.2 |
| 5,718,724 A | 2/1998 | Goicoechea et al. ........... 606/1 |
| 5,725,572 A * | 3/1998 | Lam et al. ................. 623/1.16 |
| 5,735,893 A | 4/1998 | Lau et al. ...................... 623/1 |
| 5,755,781 A | 5/1998 | Jayaraman ..................... 623/1 |
| 5,776,161 A | 7/1998 | Globerman ................. 606/194 |
| 5,776,180 A | 7/1998 | Goicoechea et al. ........... 606/1 |
| 5,776,183 A | 7/1998 | Kanesaka et al. .............. 623/1 |
| 5,800,508 A | 9/1998 | Goicoechea et al. ........ 606/108 |
| 5,800,521 A * | 9/1998 | Orth .......................... 606/195 |
| 5,855,600 A | 1/1999 | Alt ................................. 623/1 |
| 5,860,999 A * | 1/1999 | Schnepp-Pesch et al. ... 606/194 |
| 5,876,432 A | 3/1999 | Lau et al. ....................... 623/1 |
| 5,902,317 A | 5/1999 | Kleshinski et al. .......... 606/198 |
| 5,913,895 A | 6/1999 | Burpee et al. .................. 623/1 |
| 5,916,263 A | 6/1999 | Goicoechea et al. ........... 606/1 |
| 5,922,021 A | 7/1999 | Jang ............................... 623/1 |
| 5,935,161 A * | 8/1999 | Robinson et al. ........... 606/195 |
| 5,938,696 A | 8/1999 | Goicoechea et al. ........... 606/1 |
| 5,954,743 A * | 9/1999 | Jang .......................... 623/1.15 |
| 5,972,018 A * | 10/1999 | Israel et al. ................ 623/1.15 |
| 6,013,854 A | 1/2000 | Moriuchi .................... 606/194 |
| 6,051,020 A | 4/2000 | Goicoechea et al. ........... 623/1 |
| 6,090,127 A | 7/2000 | Globerman ................. 606/194 |
| 6,106,548 A | 8/2000 | Roubin et al. .............. 623/1.15 |
| 6,129,755 A | 10/2000 | Mathis et al. .............. 623/1.15 |
| 6,156,052 A * | 12/2000 | Richter et al. .............. 606/198 |
| 6,273,911 B1 | 8/2001 | Cox et al. .................. 623/1.15 |
| 6,348,065 B1 | 2/2002 | Brown et al. .............. 623/1.16 |
| 6,451,052 B1 | 9/2002 | Burmeister et al. ........ 623/1.16 |
| 6,464,722 B2 | 10/2002 | Israel et al. ................ 623/1.17 |
| 6,582,461 B1 | 6/2003 | Burmeister et al. ........ 623/1.18 |
| 6,596,022 B2 | 7/2003 | Lau et al. ................... 623/1.16 |
| 6,818,014 B2 * | 11/2004 | Brown et al. .............. 623/1.16 |
| 2001/0056298 A1 | 12/2001 | Brown et al. .............. 623/1.16 |
| 2002/0007212 A1 | 1/2002 | Brown et al. .............. 623/1.16 |
| 2002/0177893 A1 | 11/2002 | Brown et al. .............. 623/1.16 |
| 2004/0230294 A1 * | 11/2004 | Fischell et al. ............. 623/1.16 |

FOREIGN PATENT DOCUMENTS

EP      0 540 290 A2    5/1993

| EP | 0 541 443 A1 | 5/1993 |
| EP | 0 606 165 A1 | 7/1994 |
| JP | 6-4175 | 3/1994 |
| WO | WO 94/17754 | 8/1994 |
| WO | WO-00/28922 * | 5/2000 |

OTHER PUBLICATIONS

*A View of A Vascular Stents*, by Richard A. Schatz, MD, From the Arizona Heart Institute Foundation, Phoenix, Arizona, *CIRCULATION*, vol. 79, No. 2, Feb. 1989, pp. 445-457.

*The Self-Expanding Mesh Stent*, by Ulrich Sigwart, *SECTION IV*, Chapter 29, pp. 605-610.

Japanese Infringement Search on Articulated Expandable Stents, Dated Jul. 12, 1995.

*Engineering Fluid Mechanics, Third Edition*, John A. Roberson and Clayton T. Crowe, pp. 94 and pp. 414-421.

*Cambridge Dictionary of Science and Technology*, Cambridge University Pressp. 128.

*Improved Dilation Catheter Balloons*, by Stanley B. Levy, Ph.D., *Journal Of Clinical Engineering*, vol. 11, No. 4, Jul.-Aug. 1986, pp. 291-296.

*Self-expanding Stainless Steel Biliary Stents*[1], By Harold G. Coons, MD, *RADIOLOGY 1989*, vol. 170, No. 3, Part 2, pp. 979-983.

Technical Note Entitled *Modifications of Gianturco Expandable Wire Stents*, By Barry T. Uchida et al., *AJR*, vol. 150, May 1988, pp. 1185-1187.

Brochure from Cook Incorporated regarding Gianturco-Rosch Biliary Z-Stents™.

*Expandable Biliary Endoprosthesis: An Experimental Study*, By Carrasco et al., *AJR*, vol. 145, Dec. 1985, pp. 1279-1282.

*Gianturco Expandable Metallic Biliary Stents: Results of a European Clinical Trial*[1], By Irving, et al., *Interventional Radiology*, vol. 172, No. 2, Aug. 1989, pp. 321-326.

*Tracheobronchial Tree: Expandable Metallic Stents Used in Experimental and Clinical Applications*[1], *Work In Progress*, By Wallace et al., *RADIOLOGY*, Feb. 1986, pp. 309-312.

Brochure Entitled *Ave Micro Stent*™, Instructions for Use, By Applied Fascular Engineering, Inc., pp. 1-15.

Brochure Entitled *Micro Stent*™, By Applied Vascular Engineering, Inc.

U.S. Appl. No. 08/396,569, filed Mar. 1, 1995, Brown.
U.S. Appl. No. 08/511,076, filed Aug. 3, 1995, Brown et al.
U.S. Appl. No. 09/197,278, filed Nov. 20, 1998, Brown et al.
U.S. Appl. No. 09/599,674, filed Jun. 22, 2000, Brown et al.

Starck, E/, First Clinical Experience with the Memotherm Vascular Stent:, *STENTS State of the Art Future Developments*, pp. 59-62 (Jun. 1995).

Melzer, A. et al., Performance Improvement of Surgical Instrumentation Through the Use of Ni-Ti Materials, Proceedings of *SMST-94 The First International Conference on Shape Memory and Superelastic Technologies*, pp. 401-409 (Mar. 7-10, 1994).

* cited by examiner

LONGITUDINALLY FLEXIBLE EXPANDABLE STENT

This application is a continuation of U.S. application Ser. No. 09/122,431 filed on Jul. 24, 1998, now U.S. Pat. No. 6,348,065, which is a continuation of U.S. application Ser. No. 08/511,076, filed Aug. 3, 1995, now U.S. Pat. No. 6,818,014, which is a continuation-in-part of U.S. application Ser. No. 08/396,569, filed Mar. 1, 1995, now abandoned, the entire contents of all of which are incorporated herein in their entirety by reference.

FIELD OF THE INVENTION

This invention relates to an endoprosthesis device for implantation within a body vessel, typically a blood vessel. More specifically, it relates to a tubular expandable stent of improved longitudinal flexibility.

BACKGROUND OF THE INVENTION

Stents are placed or implanted within a blood vessel for treating stenoses, strictures or aneurysms therein. They are implanted to reinforce collapsing, partially occluded, weakened, or dilated sections of a blood vessel. They have also been implanted in the urinary tract and in bile ducts.

Typically, a stent will have an unexpanded (closed) diameter for placement and an expanded (opened) diameter after placement in the vessel or the duct. Some stents are self-expanding and some are expanded mechanically with radial outward force from within the stent, as by inflation of a balloon.

An example of the latter type is shown in U.S. Pat. No. 4,733,665 to Palmaz, which issued Mar. 29, 1988, and discloses a number of stent configurations for implantation with the aid of a catheter. The catheter includes an arrangement wherein a balloon inside the stent is inflated to expand the stent by plastically deforming it, after positioning it within a blood vessel.

A type of self-expanding stent is described in U.S. Pat. No. 4,503,569 to Dotter which issued Mar. 12, 1985, and discloses a shape memory stent which expands to an implanted configuration with a change in temperature. Other types of self-expanding stents not made of shape memory material are also known.

This invention is directed to stents of all these types when configured so as to be longitudinally flexible as described in detail hereinbelow. Flexibility is a desirable feature in a stent so as to conform to bends in a vessel. Such stents are known in the prior art. Examples are shown in U.S. Pat. No. 4,856,516 to Hillstead; U.S. Pat. No. 5,104,404 to Wolff; U.S. Pat. No. 4,994,071 to MacGregor; U.S. Pat. No. 5,102,417 to Palmaz; U.S. Pat. No. 5,195,984 to Schatz; U.S. Pat. No. 5,135,536 to Hillstead; U.S. Pat. No. 5,354,309 to Shepp-Pesch et al.; EPO. Patent. Application 0 540 290 Å2 to Lau; EPO. Patent. Application. No. 0 364 787 B1 to Schatz, and PCT. Application WO 94/17754 (also identified as German Patent Application 43 03 181).

Generally speaking, these kinds of stents are articulated and are usually formed of a plurality of aligned, expandable, relatively inflexible, circular segments which are interconnected by flexible elements to form a generally tubular body which is capable of a degree of articulation or bending. Unfortunately, a problem with such stents is that binding, overlapping or interference can occur between adjacent segments on the inside of a bend due to the segments moving toward each other and into contact or on the outside of a bend the segments can move away from each other, leaving large gaps. This can lead to improper vessel support, vessel trauma, flow disturbance, kinking, balloon burst during expansion, and difficult recross for devices to be installed through already implanted devices and to unsupported regions of vessel.

A diamond configuration with diagonal connections between each and every diamond of each segment is also known but such closed configurations lack flexibility.

It is an object of this invention to provide a longitudinally flexible stent of open configuration that avoids these problems and exhibits improved flexibility (radially and longitudinally) in the stent body segments thereof rather than in flexible joints between the segments.

SUMMARY OF THE INVENTION

To this end, the invention provides a tubular expandable stent, comprising: a plurality of cylindrical shaped open cylindrical segments aligned on a common longitudinal axis to define a generally tubular stent body, each segment being defined by a member formed in an undulating flexible pattern of interconnected substantially parallel struts with pairs thereof having alternating interconnecting end portions to define the periphery of the expandable stent segment, and in which the connected end portions of paired struts in each segment, before the stent is expanded, are positioned substantially opposite to connected end portions of paired struts in adjacent segments. The segments are interconnected by a plurality of interconnecting elements extending from some of the connected end portions on one segment to some of the connected end portions on adjacent segments in such a manner that there are three or more legs between points of connection from one side of each segment to its other side. Additionally, the connecting elements extend angularly from connecting end portion of one segment to connecting end portion of an adjacent segment, not to an opposite connecting end portion on an adjacent segment, whereby upon expansion of the stent the adjacent segments are displaced relative to each other about the periphery of the stent body to accommodate flexing of the stent within paired struts without interference between adjacent segments, rather than by means of articulating flexible connectors between segments. As a result, the connectors id between the segments are not intended to flex or bend under normal use.

BEST MODE DESCRIPTION OF THE INVENTION

Figure 1:
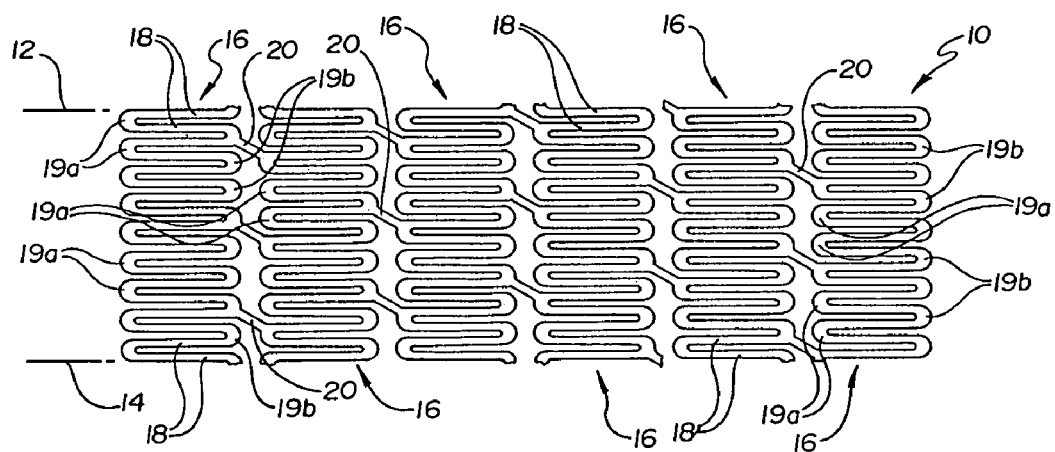
FIG. 1 shows a flat view of an unexpanded stent configuration according to the invention.
Figure 2:
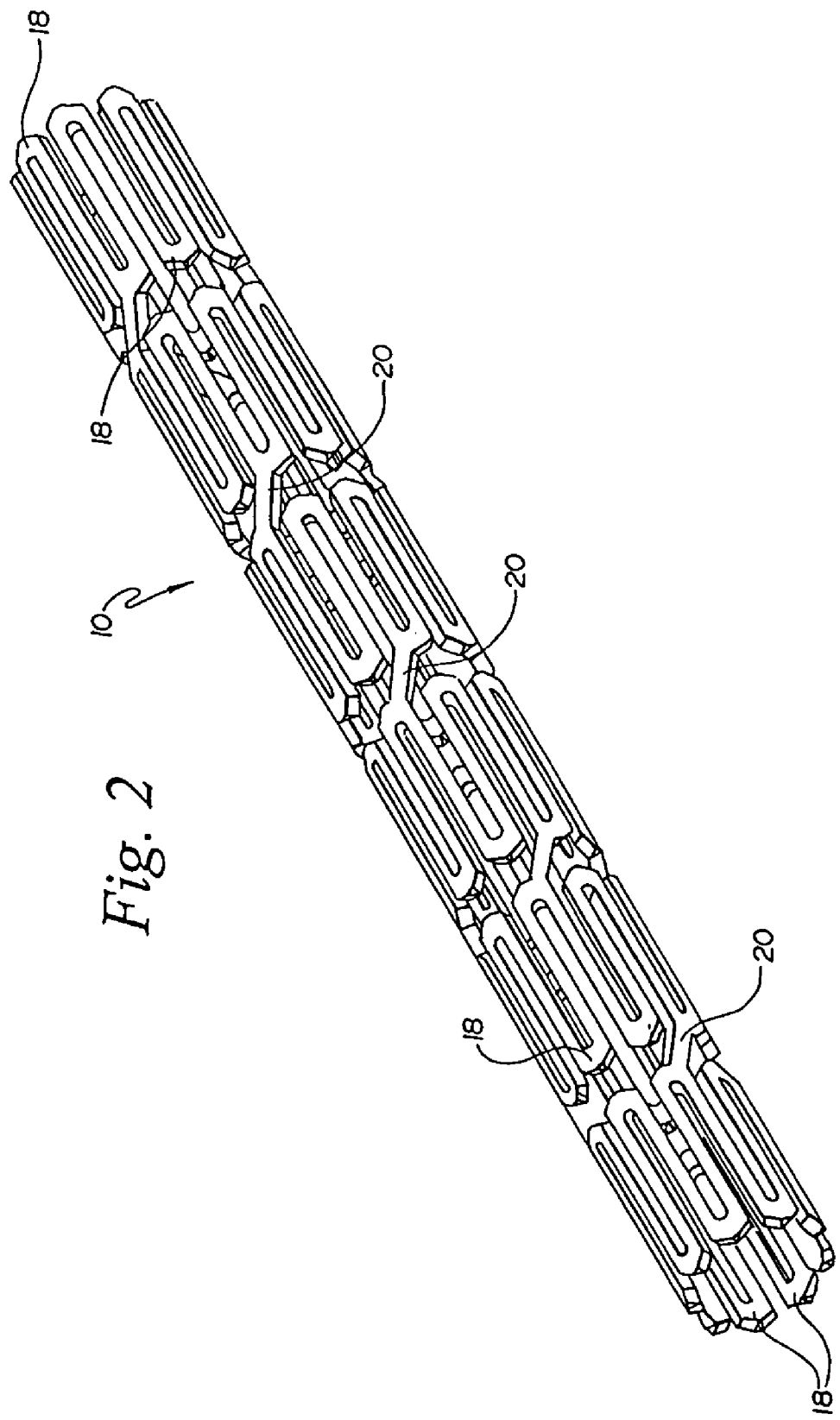
FIG. 2 shows the pattern of FIG. 1 in a tubular, unexpanded stent.

Turning to the Figures, FIG. 1 and FIG. 2 show a fragmentary flat view of an unexpanded stent configuration and the actual tubular stent (unexpanded), respectively. That is, the stent is shown for clarity in FIG. 1 in the flat and may be made from a flat pattern 10 (FIG. 1) which is formed into a tubular shape by rolling the pattern so as to bring edges 12 and 14 together (FIG. 1). The edges may then joined as by welding or the like to provide a configuration such as that shown in FIG. 2.

The configuration can be seen in these Figures to be made up of a plurality of adjacent segments generally indicated at 16, each of which is formed in an undulating flexible pattern of substantially parallel struts 18. Pairs of struts are interconnected at alternating end portions 19a and 19b. As is seen in FIG. 1, the interconnecting end portions 19b of one segment are positioned opposite interconnecting end portions 19a of adjacent segments. The end portions as shown are generally elliptical but may be rounded or square or pointed or the like. Any configuration of end portions is acceptable so long as it provides an undulating pattern, as shown. When the flat form 10 is formed into an unexpanded tube as shown in FIG. 2, the segments are cylindrical but the end portions 19 of adjacent segments remain in an opposed position relative to each other.

A more preferred method of manufacture begins with a thin walled tube which is then laser cut to provide the desired configuration. It may also be chemically etched or EDM'd (electrical discharge machined) to form an appropriate configuration.

Interconnecting elements 20 extend from one end portion 19 of one segment 16 to another end portion 19 of another adjacent segment 16 but not to an oppositely positioned end portion 19 of an adjacent segment 16. There are at least three struts included between the points on each side of a segment 16 at which an interconnecting element 20 contacts an end portion 19. This results in the interconnecting elements 20 extending in an angular direction between segments around the periphery of the tubular stent. Interconnecting elements 20 are preferably of the same length but may vary from one segment to the other. Also, the diagonal direction may reverse from one segment to another extending upwardly in one case and downwardly in another, although all connecting elements between any pair of segments are substantially parallel. FIG. 1, for example shows them extending downwardly, right to left. Upwardly would extend up left to right in this configuration.

Figure 3:
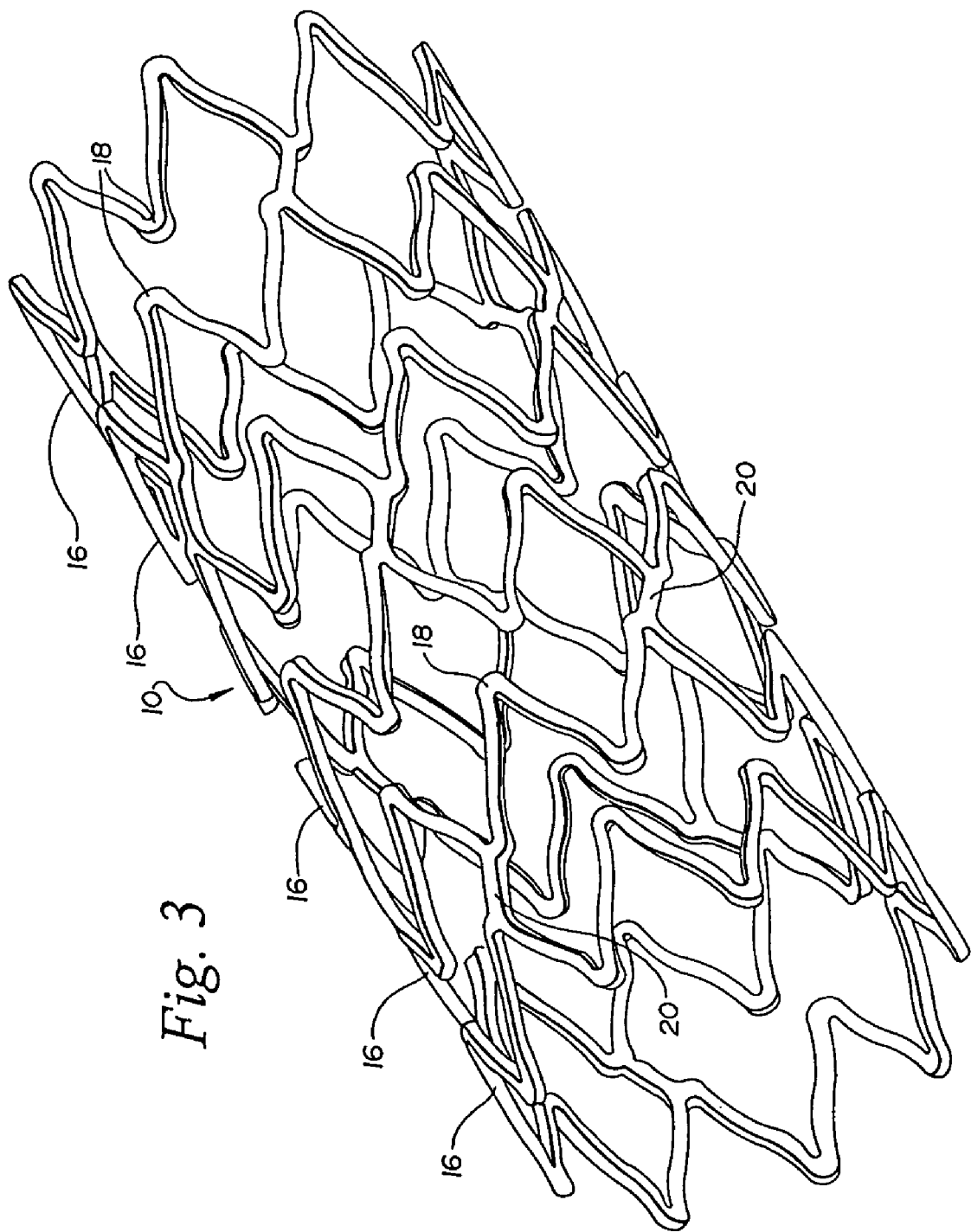
FIG. 3 shows an expanded stent of the configuration shown in FIG. 1.

As a result of this angular extension of the interconnecting elements 20 between adjacent segments and loops, upon expansion of the stent as seen in FIG. 3, the closest adjacent end portions 19 between segments 16 are displaced from each other and are no longer opposite each other so as to minimize the possibility of binding or overlapping between segments, i.e., pinching.

The number of interconnecting elements 20 may vary depending on circumstances in any particular instance. Three per segment are satisfactory for the configuration shown and at least three will be used typically.

Figure 4:
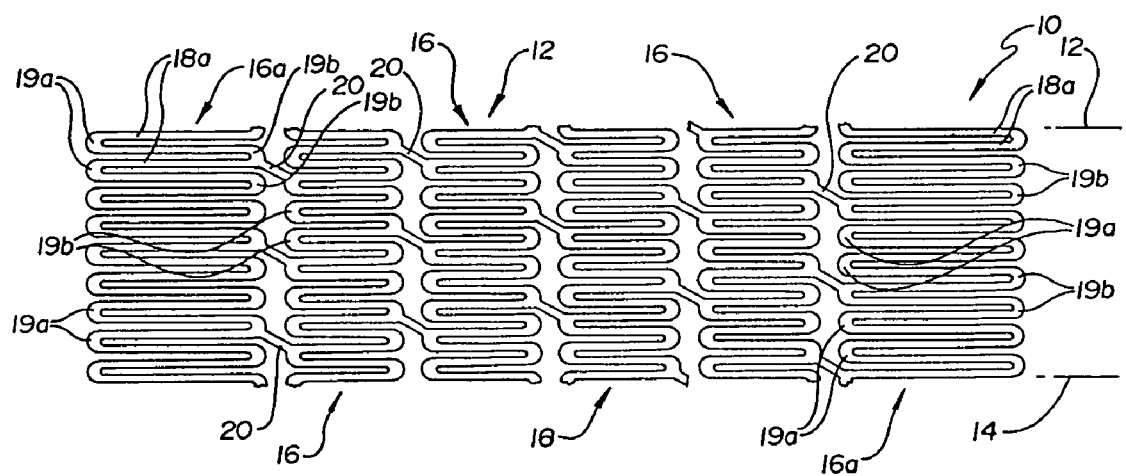
FIG. 4 shows a flat view of an alternate unexpanded stent configuration according to the invention.

The alternate design shown in FIG. 4 includes longer struts 18a in the two end segments 16a than in the intermediate segments 16. This allows the end segments (16a) to have less compression resistance than the intermediate segments (16), providing a more gradual transition from the native vessel to the support structure of the stent. Otherwise, the configuration is the same as that shown in FIG. 1.

As already indicated, this invention is applicable to self-expanding configurations, mechanically expandable configurations and to a wide variety of materials, including both metal and plastic and any other material capable of functioning as an expandable stent. For example, the stent may be of metal wire or ribbon such as tantalum, stainless steel or the like. It may be thin-walled. It may be of shape memory alloy such as Nitinol or the like, etc.

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. A tubular, flexible, expandable stent having a proximal end and a distal end and comprising:
   a plurality of cylindrical shaped segments aligned on a common longitudinal axis to define a generally tubular stent body, each segment having a proximal end and a distal end, each segment being defined by an undulating pattern of interconnected struts to define the periphery of the stent body, circumferentially adjacent struts interconnected at only one end of the struts; and
   a plurality of interconnecting elements, each interconnecting element extending from an interconnected end of adjacent strut on one segment to a circumferentially offset interconnected end of adjacent struts on an adjacent segment, each interconnecting element having a proximal end and a distal end, the distal end offset in a circumferential direction and in a longitudinal direction from the proximal end;
   the stent including cylindrical shaped segments which have interconnecting elements extending from the distal end of the segment and from the proximal end of the segment, each interconnecting element which extends from the distal end of the segment connected to an interconnecting element which extends from the proximal end of the segment via three struts of the segment;
   the stent further including end segments and intermediate segments, each of the struts of the end segments being longer than the struts of the intermediate segments of the stent;
   whereby, upon expansion of the stent, struts of adjacent segments are displaced relative to each other about the periphery of the stent body to accommodate longitudinal flexing of the stent within the segments and without interference between adjacent segments.

2. A substantially cylindrically shaped stent having a longitudinal axis,
   the stent comprising a plurality of closed undulating segments, the undulating segments extending circumferentially about the stent,
   each undulating segment having a first end and a second end, the first end characterized by a plurality of end portions separated by gaps, the second end characterized by a plurality of end portions separated by gaps, the gaps on the first end circumferentially offset from the gaps on the second end and the end portions on the first end circumferentially offset from the end portions on the second end,
   one of the undulating segments located at a first end of the stent having a plurality of interconnecting elements extending from one end of the segment only to a segment adjacent thereto and one of the undulating segments located at a second end of the stent having a plurality of interconnecting elements extending from one end of the undulating segment only to an undulating segment adjacent thereto,
   there being a plurality of intermediate undulating segments which are located the segments at the first and second ends of the stent, each intermediate undulating segment having interconnecting elements extending from the first and second ends of the intermediate undulating segments, the interconnecting elements extending from less than all of the end portions at both ends of the intermediate undulating segments, each interconnecting element extending from an end portion of an undulating segment to an end portion of an undulating segment adjacent thereto, each interconnecting element having a proximal end and a distal end, the distal end being offset in both a circumferential direction and a longitudinal direction from the proximal end.

3. A tubular, flexible, expandable stent having a proximal end and a distal end and a sidewall with a plurality of openings therethrough, the stent comprising:

a plurality of cylindrical shaped segments aligned on a common longitudinal axis to define a generally tubular stent body, each segment being defined by an undulating pattern of interconnected struts to define the periphery of the stent body, circumferentially adjacent struts interconnected at only one end of the struts; and a plurality of interconnecting elements, each interconnecting element extending from an interconnected end of circumferentially adjacent struts on one segment to an interconnected end of circumferentially adjacent struts on an adjacent segment, each interconnecting element having a proximal end and a distal end, the distal end circumferentially and longitudinally offset from the proximal end;

the stent including cylindrical shaped segments having at least three struts extending between each interconnecting element extending distally from the cylindrical shaped segment and the nearest interconnecting element extending proximally from the cylindrical shaped segment, wherein each of the openings in the sidewall is bounded by two interconnecting elements and portions of two different adjacent cylindrical shaped segments.

4. A tubular, flexible, expandable stent, comprising:

a plurality of cylindrical shaped segments aligned on a common longitudinal axis, each segment having a proximal end and a distal end and being defined by a member formed in a closed undulating pattern of interconnected struts, circumferentially adjacent struts interconnected at only one end of the struts at an interconnected end portion and a plurality of interconnecting elements each extending from one segment to an adjacent segment, some of the segments having interconnecting elements extending from the distal end of the segment and from the proximal end of the segment, the interconnecting elements which extend from the distal end of the segment connected to the interconnecting elements which extend from the proximal end of the segment via three struts of the segment, each interconnecting element extending from one interconnected end portion of one segment to another interconnected end portion of another adjacent segment but not to an oppositely positioned end portion of an adjacent segment.

5. A substantially cylindrically shaped stent having a longitudinal axis, the stent comprising a plurality of closed undulating segments, the undulating segments extending circumferentially about the stent, each undulating segment having a first end and a second end, the first end characterized by a plurality of end portions separated by gaps, the second end characterized by a plurality of end portions separated by gaps, the gaps on the first end circumferentially offset from the gaps on the second end and the end portions on the first end circumferentially offset from the end portions on the second end, an undulating segment at a first end of the stent having a plurality of interconnecting elements extending from one end of the segment only to a segment adjacent thereto and an undulating segment at a second end of the stent having a plurality of interconnecting elements extending from one end of the undulating segment only to an undulating segment adjacent thereto, a plurality of undulating segments which are located between the segments at the first and second ends of the stent having interconnecting elements extending from less than all of the end portions at both ends of the segments, each interconnecting element having a proximal end extending from an end portion of one undulating segment and a distal end extending from an end portion of an undulating segment adjacent to said one undulating segment, each interconnecting element having a proximal end and a distal end, the distal end circumferentially and longitudinally offset from the proximal end, the interconnecting elements oriented diagonally to the longitudinal axis of the stent.

6. The stent of claim 3 wherein each interconnecting element is substantially straight.

7. The stent of claim 3 wherein the stent further includes end segments and intermediate segments and the end segments of the stent include longer struts than the intermediate segments of the stent.

8. The stent of claim 3 comprising interconnecting elements which are circumferentially adjacent one another and are separated from one another by six struts on each of the cylindrical shaped segments from which they extend.

9. The stent of claim 5 wherein the stent is made of metal.

10. The stent of claim 9 wherein the metal is a shape memory alloy.

11. The stent of claim 5 wherein the stent forms a thin-walled tubular member.

12. The stent of claim 5 formed as a self-expanding configuration.

13. The stent of claim 5 formed as a mechanically expandable configuration.

14. The stunt of claim 5 wherein the interconnecting elements between adjacent segments are of the same length.

15. The stent of claim 3 wherein the stent is expandable from an unexpanded state to an expanded state, in the unexpanded state at least a portion of the interconnected struts being parallel to one another.

16. The stent of claim 3 constructed and arranged to be self-expanding.

17. The stent of claim 3 constructed and arranged to be balloon expandable.

18. The stent of claim 3 wherein the stent is constructed from a shape memory material.

19. The stent of claim 3 wherein the end portions of adjacent cylindrical shaped segments are not longitudinally opposite one another.

* * * * *

UNITED STATES PATENT AND TRADEMARK OFFICE
CERTIFICATE OF CORRECTION

PATENT NO.        : 6,981,986 B1                                           Page 1 of 1
APPLICATION NO.   : 09/666866
DATED             : January 3, 2006
INVENTOR(S)       : Brian J. Brown and Michael L. Davis It is certified that error appears in the above-identified patent and that said Letters Patent is hereby corrected as shown below:

In column 4, line 66, claim 2, insert --between-- after "located" and before "the".

Signed and Sealed this

Twenty-sixth Day of October, 2010

David J. Kappos
*Director of the United States Patent and Trademark Office*